United States Patent [19]

Sonoda et al.

[11] 4,346,235
[45] Aug. 24, 1982

[54] FLUORINE-CONTAINING COMPOUNDS

[75] Inventors: Noboru Sonoda, Osaka; Shinji Murai, Kawanishi; Kazuhisa Takii, Nagaokakyo, all of Japan

[73] Assignees: Okamura Oil Mill Limited; Daikin Kogyo Co., Ltd., both of Japan

[21] Appl. No.: 158,301

[22] Filed: Jun. 10, 1980

[30] Foreign Application Priority Data

Jun. 15, 1979 [JP] Japan .................................. 54-75826
Jun. 15, 1979 [JP] Japan .................................. 54-75827

[51] Int. Cl.³ ...................... C07C 55/02; C07C 53/21
[52] U.S. Cl. ............................... 562/596; 252/174.19; 252/356; 260/408; 526/245; 526/252; 526/253; 526/255; 528/299; 560/192; 560/219; 560/227; 562/595; 562/598; 562/605
[58] Field of Search ................ 260/408; 560/192, 227, 560/219; 562/605, 596, 595, 598

[56] References Cited

U.S. PATENT DOCUMENTS

| | | | |
|---|---|---|---|
| 2,411,158 | 11/1946 | Hanford | 562/605 |
| 2,559,628 | 7/1951 | Joyce | 568/842 |
| 2,811,551 | 10/1957 | Coffman et al. | 560/192 |
| 2,870,200 | 1/1959 | Kharasch et al. | 560/192 |
| 2,951,051 | 8/1960 | Tiers | 260/408 |
| 3,819,668 | 6/1974 | Jaeger | 560/227 |

Primary Examiner—Natalie Trousof
Assistant Examiner—Vera C. Clarke
Attorney, Agent, or Firm—Larson and Taylor

[57] ABSTRACT

A novel fluorine-containing compound of the formula $$R_1-A-R_2$$

wherein
A is

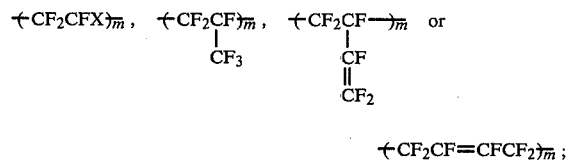

$$(CF_2CF=CFCF_2)_{\overline{m}};$$

$R_1$ and $R_2$ are each hydrogen or $R_3OOC(CH_2)_{\overline{n}}$, while $R_1$ and $R_2$ may not be hydrogen at the same time; X is hydrogen or halogen; $R_3$ is hydrogen or a lower alkyl group; m is an integer of 1 to 5; and n is an integer of 4 to 11, and a process for preparing the same.

3 Claims, No Drawings

FLUORINE-CONTAINING COMPOUNDS

This invention relates to fluorine-containing compounds and more particularly to fluorine-containing carboxylic acids and esters thereof and to a process for preparing the same.

The fluorine-containing compounds of this invention are those represented by the formula $$R_1-A-R_2 \qquad (I)$$

wherein A is

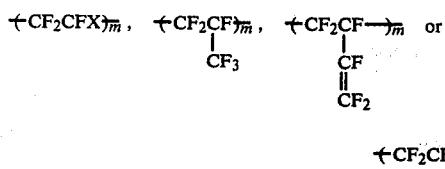

$$-(CF_2CF=CFCF_2)_{\overline{m}};$$

$R_1$ and $R_2$ are each hydrogen or $R_3OOC-(CH_2)_n$, while $R_1$ and $R_2$ may not be hydrogen at the same time; X is hydrogen or halogen; $R_3$ is hydrogen or a lower alkyl group; m is an integer of 1 to 5; and n is an integer of 4 to 11.

The fluorine-containing compounds of this invention and esters thereof are novel compounds which we have developed for the first time and which are not described in any literature.

The compounds prepared by oxidizing a telomer of tetrafluoroethylene and methanol are known as fluorine-containing carboxylic acids. These conventional compounds have carboxyl groups linked directly with fluorine-containing groups. Such known carboxylic acids or esters thereof are chemically unstable in a considerable degree. Further the esters thereof are susceptible to hydrolysis and these disadvantages seriously restrict the use of the prior art esters thereof. On the other hand, the compounds of this invention have long-chain methylene groups positioned between the carboxyl groups and the fluorine-containing functional groups and thus are essentially different in chemical structure from the conventional fluorine-containing carboxylic acid compounds. No compound has been known heretofore in which long-chain methylene groups are present between fluorine-containing groups and carboxyl groups. The novel compounds of this invention are remarkably superior in chemical stabilities to conventional carboxylic acid compounds. Moreover, the esters of this invention are conspicuously stable against hydrolysis and therefore find wide applications, because stable carboxyl groups can be utilized.

The novel fluorine-containing compounds of this invention have remarkable emulsifying properties and can be used singly as an emulsifier. The present compounds are also usable as an intermediate for the preparation of synthetic resins. The synthetic resins thus prepared have excellent emulsifying properties and thus are well suitable for use in the preparation of emulsion coating compositions.

Table 1 below gives typical examples of the fluorine-containing carboxylic acids of this invention and their esters.

TABLE 1

| 1. | $CH_3OC-(CH_2)_5-CF_2-CF-H$ with ‖O and ‖CF_3 | (7-di-8-monofluoro)-9-trifluoro-pelargonic acid methyl |
|---|---|---|
| 2. | $CH_3OC-(CH_2)_5-CF_2-CF-(CH_2)_5-COCH_3$ with carbonyls and CF_3 | (7-di-8-monofluoro)-8-trifluoromethyl-tetradecadiacid dimethyl |
| 3. | $HOC-(CH_2)_5-CF_2-CF-H$ with ‖O and CF_3 | (7-di-8-monofluoro)-9-trifluoro-pelargonic acid |
| 4. | $HOC-(CH_2)_5-CF_2-CF-(CH_2)_5-COH$ with CF_3 | (7-di-8-monofluoro)-8-trifluoromethyl-tetradecadiacid |
| 5. | $CH_3OC-(CH_2)_5-CF_2CHF-H$ | 7-di-8-monofluorooctanoic acid methyl |
| 6. | $CH_3OC-(CH_2)_5-(CF_2CHF)_{\overline{2}}H$ | 7,9-di-8,10-monofluorodecanoic acid methyl |
| 7. | $CH_3OC-(CH_2)_5-(CF_2CHF)_{\overline{3}}H$ | 7,9,11-di-8,10,12-monofluorododecanoic acid methyl |
| 8. | $CH_3OC-(CH_2)_5-CF_2CHF-(CH_2)_5-COCH_3$ | 7-di-8-monofluorotetradecadiacid dimethyl |
| 9. | $CH_3OC-(CH_2)_5-(CF_2CHF)_2-(CH_2)_5-COCH_3$ | 7,9-di-8,10-monofluorohexadecadiacid dimethyl |
| 10. | $CH_3OC-(CH_2)_5-(CF_2CHF)_3-(CH_2)_5-COCH_3$ | 7,9,11-di-8,10,12-monofluoro-octadecadiacid dimethyl |

TABLE 1-continued

| # | Structure | Name |
|---|---|---|
| 11. | HOC(O)—(CH$_2$)$_5$—CF$_2$CHF—H | 7-di-8-monofluorooctanoic acid |
| 12. | HOC(O)—(CH$_2$)$_5$—(CF$_2$CHF)$_2$—H | 7,9-di-8,10-monofluorodecanoic acid |
| 13. | HOC(O)—(CH$_2$)$_5$—(CF$_2$CHF)$_3$—H | 7,9,11-di-8,10,12-monofluorododecanoic acid |
| 14. | HOC(O)—(CH$_2$)$_5$—CF$_2$CHF—(CH$_2$)$_5$—COH(O) | 7-di-8-monofluorotetradecadiacid |
| 15. | HOC(O)—(CH$_2$)$_5$—(CF$_2$CHF)$_2$—(CH$_2$)$_5$—COH(O) | 7,9-di-8,10-monofluorohexadecadiacid |
| 16. | HOC(O)—(CH$_2$)$_5$—(CF$_2$CHF)$_3$—(CH$_2$)$_5$—COH(O) | 7,9,11-di-8,10,12-monofluorooctadecadiacid |
| 17. | CH$_3$OC(O)—(CH$_2$)$_5$—CF$_2$CF$_2$—H | 7,8-difluorooctanoic acid methyl |
| 18. | CH$_3$OC(O)—(CH$_2$)$_5$—(CF$_2$CF$_2$)$_2$—H | 7,8,9,10-difluorodecanoic acid methyl |
| 19. | CH$_3$OC(O)—(CH$_2$)$_5$—(CF$_2$CF$_2$)$_3$—H | 7,8,9,10,11,12-difluorododecanoic acid methyl |
| 20. | CH$_3$OC(O)—(CH$_2$)$_5$—CF$_2$CF$_2$—(CH$_2$)$_5$—COCH$_3$(O) | 7,8-difluorotetradecadiacid dimethyl |
| 21. | CH$_3$OC(O)—(CH$_2$)$_5$—(CF$_2$CF$_2$)$_2$—(CH$_2$)$_5$—COCH$_3$(O) | 7,8,9,10-difluorohexadecadiacid dimethyl |
| 22. | CH$_3$OC(O)—(CH$_2$)$_5$—(CF$_2$CF$_2$)$_3$—(CH$_2$)$_5$—COCH$_3$(O) | 7,8,9,10,11,12-difluorooctadecadiacid dimethyl |
| 23. | HOC(O)—(CH$_2$)$_5$—CF$_2$CF$_2$—H | 7,8-difluorooctanoic acid |
| 24. | HOC(O)—(CH$_2$)$_5$—(CF$_2$CF$_2$)$_2$—H | 7,8,9,10-difluorodecanoic acid |
| 25. | HOC(O)—(CH$_2$)$_5$—(CF$_2$CF$_2$)$_3$—H | 7,8,9,10,11,12-difluorododecanoic acid |
| 26. | HOC(O)—(CH$_2$)$_5$—CF$_2$CF$_2$—(CH$_2$)$_5$—COH(O) | 7,8-difluorotetradecadiacid |
| 27. | HOC(O)—(CH$_2$)$_5$—(CF$_2$CF$_2$)$_2$—(CH$_2$)$_5$—C(O)—OH | 7,8,9,10-difluorohexadecadiacid |
| 28. | HOC(O)—(CH$_2$)$_5$—(CF$_2$CF$_2$)$_3$—(CH$_2$)$_5$—COH(O) | 7,8,9,10,11,12-difluorooctadecadiacid |
| 29. | CH$_3$OC(O)—(CH$_2$)$_5$—CF$_2$CFClH | 7,7,8-trifluoro-8-chlorooctanoic acid methyl |
| 30. | CH$_3$OC(O)—(CH$_2$)$_5$(CF$_2$CFCl)$_2$H | 7,7,8,9,9,10-hexafluoro-8,10-dichlorodecanoic acid methyl |

TABLE 1-continued

| # | Structure | Name |
|---|---|---|
| 31. | CH₃OC—(CH₂)₅—(CF₂CFCl)₃—H<br>‖<br>O | 7,7,8,9,9,10,11,11,12-nonylfluoro-8,10,12-trichlorododecanoic acid methyl |
| 32. | CH₃OC—(CH₂)₅—CF₂CFCl(CH₂)₅—COCH₃<br>‖ ‖<br>O O | 7,7,8-trifluoro-8-chlorotetradecadiacid dimethyl |
| 33. | CH₃OC—(CH₂)₅—(CF₂CFCl)₂—(CH₂)₅—COCH₃<br>‖ ‖<br>O O | 7,7,8,9,9,10-hexafluoro-8,10-dichlorotetradecadiacid dimethyl |
| 34. | CH₃OC—(CH₂)₅—(CF₂CFCl)₃—(CH₂)₅—COCH₃<br>‖ ‖<br>O O | 7,7,8,9,9,10,11,11,12-nonylfluoro-8,10,12-trifluorotetradecadiacid dimethyl |
| 35. | HOC—(CH₂)₅—CF₂CFCl—H<br>‖<br>O | 7,7,8-trifluoro-8-chlorooctanoic acid |
| 36. | HOC—(CH₂)₅—(CF₂CFCl)₂—H<br>‖<br>O | 7,7,8,9,9,10-hexafluoro-8,10-dichlorodecanoic acid |
| 37. | HOC—(CH₂)₅—(CF₂CFCl)₃—H<br>‖<br>O | 7,7,8,9,9,10,11,11,12-nonylfluoro-8,10,12-trichlorododecanoic acid |
| 38. | HOC—(CH₂)₅—CF₂CFCl—(CH₂)₅—COH<br>‖ ‖<br>O O | 7,7,8-trifluoro-8-chlorotetradecadiacid |
| 39. | HOC—(CH₂)₅—(CF₂CFCl)₂—(CH₂)₅—COH<br>‖ ‖<br>O O | 7,7,8,9,9,10-hexafluoro-8,10-dichlorotetradecadiacid |
| 40. | HOC—(CH₂)₅—(CF₂CFCl)₃—(CH₂)₅—COH<br>‖ ‖<br>O O | 7,7,8,9,9,10,11,11,12-nonylfluoro-8,10,12-trifluorotetradecadiacid |
| 41. | CH₃OC—(CH₂)₅—CF₂CHF—H<br>‖<br>O | 7-di-8-monofluorooctanoic acid methyl |
| 42. | CH₃OC—(CH₂)₅—(CF₂CHF)₂H<br>‖<br>O | 7,9-di-8,10-monofluorodecanoic acid methyl |
| 43. | CH₃OC—(CH₂)₅—(CF₂CHF)₃H<br>‖<br>O | 7,9,11-di-8,10,12-monofluorododecanoic acid methyl |
| 44. | CH₃OC—(CH₂)₅—CF₂CHF—(CH₂)₅—COCH₃<br>‖ ‖<br>O O | 7-di-8-monofluorotetradecadiacid dimethyl |
| 45. | CH₃OC—(CH₂)₅—(CF₂CHF)₂—(CH₂)₅—COCH₃<br>‖ ‖<br>O O | 7,9-di-8,10-monofluorohexadecadiacid dimethyl |
| 46. | CH₃OC—(CH₂)₅—(CF₂CHF)₃—(CH₂)₅—COCH₃<br>‖ ‖<br>O O | 7,9,11-di-8,10,12-monofluorooctadecadiacid dimethyl |
| 47. | HOC—(CH₂)₅—CF₂CHF—H<br>‖<br>O | 7-di-8-monofluorooctanoic acid |
| 48. | HOC—(CH₂)₅—(CF₂CHF)₂H<br>‖<br>O | 7,9-di-8,10-monofluorodecanoic acid |
| 49. | HOC—(CH₂)₅—(CF₂CHF)₃H<br>‖<br>O | 7,9,11-di-8,10,12-monofluorododecanoic acid |
| 50. | HOC—(CH₂)₅—CF₂CHF—(CH₂)₅—COCH₃<br>‖ ‖<br>O O | 7-di-8-monofluorotetradecadiacid methyl |

TABLE 1-continued

| | | |
|---|---|---|
| 51. | HOC—(CH$_2$)$_5$—(CF$_2$CHF)$_2$—(CH$_2$)$_5$—COCH$_3$<br>‖<br>O                                                        ‖<br>                                                          O | 7,9-di-8,10-monofluorohexadecadiacid methyl |
| 52. | HOC—(CH$_2$)$_5$—(CF$_2$CHF)$_3$—(CH$_2$)$_5$—COCH$_3$<br>‖                                                        ‖<br>O                                                          O | 7,9,11-di-8,10,12-monofluoro-octadecadiacid methyl |
| 53. | HOC—(CH$_2$)$_5$—CF$_2$CF═CFCF$_2$—H<br>‖<br>O | 1,1,2,3,4,4-hexafluoro-9-carboxy-2-nonen |
| 54. | CH$_3$OC—(CH$_2$)$_5$—CF$_2$CF═CFCF$_2$—H<br>‖<br>O | 1,1,2,3,4,4-hexafluoro-9-carboxymethyl-2-nonen |
| 55. | HOC—(CH$_2$)$_5$—CF$_2$CF—H<br>‖                           \|<br>O                         CF<br>                             ‖<br>                             CF$_2$ | 1,1,2,3,4,4-hexafluoro-9-carboxy-1-nonen |

The novel fluorine-containing carboxylic acids of this invention and their esters and prepared by a process comprising the steps of reacting a hydrogen peroxide with a cyclic ketone of the formula

(wherein n is an integer of 4 to 11) to yield a cyclic ketone peroxide; and reacting the cyclic ketone peroxide thus prepared with a fluorine-containing olefin of the formula $$CF_2\!=\!CFR_4 \qquad (III)$$

wherein $R_4$ is hydrogen, halogen, a trifluoromethyl group or the group $CF_2\!=\!CF-$ in the presence of a ferrous salt to prepare a fluorine-containing carboxylic acid of the formula $$R_1-A-R_2 \qquad (I)$$

wherein A is

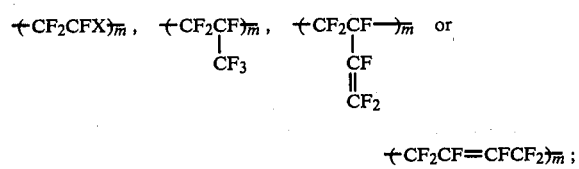

$R_1$ and $R_2$ are each hydrogen or $R_3OOC\text{-}(CH_2)_n$, while $R_1$ and $R_2$ may not be hydrogen at the same time; X is hydrogen or halogen; $R_3$ is hydrogen or a lower alkyl group; m is an integer of 1 to 5; and n is an integer of 4 to 11. Preferably the compounds of the formula (I) are obtained in which the lower alkyl group contains 1 to 4 carbon atoms.

The cyclic ketone of the formula (II) and hydrogen peroxide are reacted in an appropriate ratio which is not particularly limited but widely variable. Usually the latter is used in an amount of 0.5 to 2 moles, preferably about 1 mole, per mole of the former. Exemplary of useful cyclic ketones of the formula (II) are cyclopentanone, cyclohexanone, cycloheptanone, cyclooctanone, cyclononanone, cyclodecanone, cycloundecanone, cyclododecanone, etc. The hydrogen peroxide is used usually in the form of an aqueous solution having a concentration of about 30 to about 70%. This reaction (hereinafter referred to as "first reaction") is carried out preferably in the presence of a solvent. Typical of useful solvents are methanol, ethanol, isopropanol, n-butanol, tert-butanol or like lower alcohols, acetonitrile, benzene, dimethylformamide and the like. Among them, methanol and particularly absolute methanol are preferred. An acid catalyst may be incorporated in the aforesaid reaction mixture. The addition of the acid catalyst gives a higher yield of cyclic ketone peroxide. Examples of useful acid catalysts are sulfuric acid, hydrochloric acid, phosphoric acid and like mineral acids among which a sulfuric acid is desirable. The acid catalyst is used preferably in an amount of about 0.05 to about 0.5 mole per mole of the cyclic ketone of the formula (II). The first reaction is conducted generally at about $-70°$ to about 50° C., preferably at about $-10°$ to about 10° C., and completed usually in about 5 to about 60 minutes.

According to this invention, the cyclic ketone peroxide may be separated from the reaction mixture thus obtained and used in the subsequent reaction (hereinafter referred to as "second reaction"). Alternatively the reaction mixture per se containing the cyclic ketone peroxide therein may be subjected, as it is or as concentrated, to the second reaction. While the ratio of the cyclic ketone peroxide to the fluorine-containing olefin of the formula (III) to be used in the second reaction is not restricted to a narrow range, the latter is employed in a quantity of usually about 1 to about 8 moles, preferably about 2 to 4 moles, per mole of the former. Useful fluorine-containing olefins of the formula (III) are illustrated by trifluoroethene, tetrafluoroethene, 1-chloro-1,2,2-trifluoroethene, hexafluoropropene, hexafluorobutadiene and the like. It is desired to carry out the second reaction in the presence of a suitable solvent. The solvents useful in the first reaction are usable as the solvent in the second reaction. The second reaction is effected in the presence of a ferrous salt serving as a catalyst. Examples of useful catalysts are ferrous sulfate, ferrous chloride, ammonium ferrous sulfate and the like. The ferrous salt is used in an amount of about 0.1 to about 2 moles, preferably about 0.8 to about 1.2 moles, per mole of the cyclic ketone peroxide. A preferred mode of the reaction is as follows. A specified quantity of the fluorine-containing olefin of the formula (III) as mixed with the solvent is stirred at a temperature below the boiling point of the olefin, generally −70° to 50° C., preferably −40° to −25° C. to obtain a suspension. Then a specific amount of ferrous salt is added to the suspension, and the cyclic ketone peroxide is dropwise added to the mixture with stirring. This reaction, if conducted under nitrogen atomsphere, will produce the contemplated product in a high yield. The first reaction is completed generally in about 1 to about 7 hours.

With this invention, the cyclic ketone peroxide produced by the reaction of a cyclic ketone with a hydrogen peroxide in lower alcohol is a lower alkoxy cyclic ketone peroxide. Thus the second reaction between the same and the olefin of the formula (III) gives the present compound of the formula (I) mainly in the form of an ester (namely a compound of the formula (I) wherein $R_3$ is a lower alkyl group). Among the compounds of the formula (I), carboxylic acid compounds (i.e. those of the formula (I) wherein $R_3$ is hydrogen) are synthesized by hydrolyzing the esters in the conventional manner. When reacting the cyclic ketone with the hydrogen peroxide in a solvent other than the lower alcohol, this produces a cyclic ketone peroxide but not an ester thereof. Therefore, on subsequent reaction between the same and the olefin of the formula (III), a compound of the formula (I) is obtained in the form of a carboxylic acid (monobasic acid or dibasic acid). It follows that an ester of the formula (I) can be synthesized by the esterification of the foregoing carboxylic acid in the usual manner. With this invention, the ester of the compound of the formula (I) can be conventionally converted into another ester by ester interchange; for example, methyl esters are transformable into ethyl esters.

The compounds of this invention thus prepared are easily isolated and purified for instance by the extraction with a solvent or distillation or like conventional operation. An excess of olefin of the formula (III), solvent or the like present in the reaction product can be recovered by a simple distilling procedure and effectively reused.

This invention will be described below in greater detail with reference to Examples to which the invention is not limited.

EXAMPLE 1

A 100 ml quantity of absolute methanol is placed in a reactor cooled to a temperature of 0° to 5° C. and equipped with a stirrer. Thereto are added 14.7 g of cyclohexanone, 1.5 g of concentrated sulfuric acid and 17.0 g of a 30% aqueous solution of hydrogen peroxide. Then the mixture is stirred for 40 minutes to yield methoxycyclohexanone peroxide. A 150 ml quantity of absolute methanol is placed in another reactor equipped with a stirrer and filled with a nitrogen gas, and is cooled to a temperature of −30° C. Thereto are added 46 g of ferrous sulfate heptahydrate (FeSO$_4$.7H$_2$O) and 60 ml of liquefied hexafluoropropene to prepare a suspension. The methoxycyclohexanone peroxide solution is dropwise added to the suspension with stirring while maintaining the temperature of the suspension at −30°±2° C. After the addition thereof, the mixture is stirred for 2.5 hours and the resulting mixture is left to stand until it is brought to room temperature. The unreacted hexafluoropropene (about 45 ml) is recovered by distillation. The reaction mixture is separated into an organic layer (upper layer) and an aqueous layer (lower layer). The organic layer (30.6 g) is washed with acid and water, and dried. A fraction (light yellow to colorless) is obtained by distillation at 50° to 200° C./1.4 mmHg. The fraction is a mixture of long-chain monobasic acid, long-chain ester of monobasic acid, long-chain dibasic acid and long-chain ester of dibasic acid all of which contain fluorine. The mixture is separated into individual compounds by rectification.

Analyses by chromatography, mass spectrometry, etc. confirm the production of the following compounds.

(1) 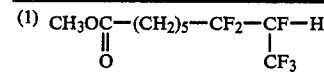

Elementary analysis (for C$_{10}$H$_{14}$O$_2$F$_6$)

|  | C | H | O | F |
|---|---|---|---|---|
| Calcd. (%) | 42.86 | 5.00 | 11.43 | 40.71 |
| Found (%) | 43.01 | 5.30 | 11.19 | 40.50 |
| IR: | 1020 cm$^{-1}$ (C—F), | | | |
|  | 1100 cm$^{-1}$–1230 cm$^{-1}$ (C—F), | | | |
|  | 1740 cm$^{-1}$ (C=O) | | | |
| $^1$HNMR (CCl$_4$): | 3.62τ(s, CH$_3$O) | | | |
|  | 0.90–2.60τ (CH$_2$ and CFH) | | | |
| Mass: m/e = | 280 (M$^+$) | | | |
|  | 249 (M$^+$—CH$_3$O) | | | |

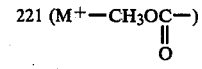

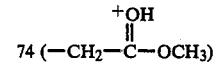

| Boiling point: | 73° C./1.4 mmHg |
|---|---|
| Yield: | 17.3 g |

(2) 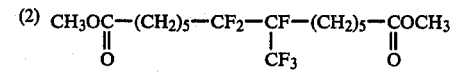

Elementary analysis

|  | C | H | O | F |
|---|---|---|---|---|
| Calcd. (%) | 50.00 | 6.37 | 15.69 | 27.94 |
| Found (%) | 50.27 | 6.30 | 15.69 | 27.74 |
| IR: | 1020 cm$^{-1}$ (C—F) | | | |
|  | 1100–1230 cm$^{-1}$ (C—F) | | | |
|  | 1740 cm$^{-1}$ (C=O) | | | |
| $^1$HNMR (CCl$_4$) | 1.2–2.1τ (bt, CH$_2$ and CFH) | | | |
|  | 2.23τ (t, CH$_2$CO, J = 6.5 Hz) | | | |
|  | 3.55τ (s, CH$_3$O) | | | |
| $^{19}$FNMR (CCl$_4$): | (CF$_3$COOH) | | | |
|  | −3.9τ (t.d, CF$_3$, J = 231 Hz, 14.7 Hz) | | | |
|  | 30.7τ (q.d, CF$_2$, J = 23.7 Hz, 6.8 Hz) | | | |
|  | 101.4τ (m) | | | |
| Mass: m/e = | 408 (M$^+$) | | | |
|  | 377 (M$^+$—CH$_3$O) | | | |

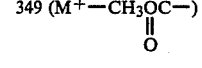

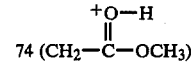

| Boiling point: | 155–156° C./0.8–1 mmHg |
|---|---|

(3) 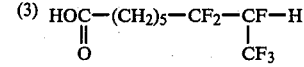

Elementary analysis

|  | C | H | O | F |
|---|---|---|---|---|
| Calcd. (%) | 40.60 | 4.51 | 12.03 | 42.86 |
| Found (%) | 40.81 | 4.52 | 11.81 | 42.68 |
| IR: | 1020 cm$^{-1}$ (C—F) | | | |

-continued

| | |
|---|---|
| | 1100–1230 cm$^{-1}$ (C—F) |
| | 1710 cm$^{-1}$ (C=O) |
| $^1$HNMR (CCl$_4$): | 11.66τ (COOH) |
| | 0.7–2.9τ (CH$_2$ and CFH) |

(4) HOC—(CH$_2$)$_5$—CF$_2$—CF—(CH$_2$)$_5$—COH
   ‖                   |                ‖
   O                  CF$_3$             O

Elementary analysis

| | C | H | O | F |
|---|---|---|---|---|
| Calcd. (%) | 47.37 | 5.79 | 16.84 | 30.00 |
| Found (%) | 47.58 | 5.70 | 16.92 | 29.80 |
| IR: | 1020 cm$^{-1}$ (C—F) | | | |
| | 1100–1230 cm$^{-1}$ (C—F) | | | |
| | 1710 cm$^{-1}$ (C=O) | | | |
| $^1$HNMR (CCl$_4$): | 10.63τ (COOH) | | | |
| | 0.5–2.7τ (CH$_2$ and CFH) | | | |

EXAMPLE 2

A 150 ml quantity of absolute methanol is placed in a reactor cooled to 0° to 5° C. and equipped with a stirrer. Thereto are added 42.0 g of cyclopentanone, 3 g of concentrated sulfuric acid and 48.6 g of a 35% aqueous solution of hydrogen peroxide. The mixture is stirred for 60 minutes to yield methoxycyclopentanone peroxide. Absolute methanol (150 ml) is placed in another reactor cooled to −40° C., equipped with a stirrer and filled with a nitrogen gas. Thereto are added 150 g of ferrous sulfate heptahydrate (FeSO$_4$.7H$_2$O) and 80 g of liquefied hexafluoropropene to prepare a suspension. The methoxycyclopentanone peroxide solution is dropwise added by degrees to the suspension with stirring while maintaining the temperature of the suspension at −40°±2° C. After the addition thereof, the mixture is stirred for 2 hours and the resulting mixture is left to stand until it is brought to room temperature. The unreacted hexafluoropropene (about 62 ml) is recovered by distillation. The reaction mixture is treated at an increased temperature of up to 40° C. and a reduced pressure of 10 to 15 mmHg to recover methanol. Then the reaction mixture is separated into an organic layer (upper layer) and an aqueous layer (lower layer). The organic layer (63.5 g) is washed with acid and water and dried. A fraction (light yellow to colorless) is obtained by distillation at 40° to 180° C./1 mmHg. The fraction is a mixture of long-chain monobasic acid, long-chain ester of monobasic acid, long-chain dibasic acid and long-chain ester of dibasic acid all of which contain fluorine. The mixture is separated into each compound by rectification.

Analyses by chromatography, mass spectrometry, etc. confirm the production of the following compounds.

(1) CH$_3$OC—(CH$_2$)$_4$—CF$_2$—CF—H
     ‖                     |
     O                    CF$_3$

Elementary analysis (for C$_9$H$_{12}$O$_2$F$_6$)

| | C | H | O | F |
|---|---|---|---|---|
| Calcd. (%) | 40.60 | 4.51 | 12.03 | 42.86 |
| Found (%) | 40.33 | 4.81 | 12.16 | 42.70 |
| IR: | 1020 cm$^{-1}$ (C—F) | | | |
| | 1100–1230 cm$^{-1}$ (C—F) | | | |
| | 1750 cm$^{-1}$ (C=O) | | | |
| $^1$HNMR (CCl$_4$): | 3.62τ (s, CH$_3$O) | | | |
| | 0.80–2.50τ (CH$_2$ and CFH) | | | |
| Mass: m/e = | 266 (M$^+$) | | | |
| | 235 (M$^+$—CH$_3$O) | | | |
| | 207 (M$^+$—CH$_3$OC—) | | | |
| |                       ‖ | | | |
| |                       O | | | |
| |          +OH | | | |
| |           ‖ | | | |
| | 74 (CH$_2$COCH$_3$) | | | |
| Boiling point: | 58° C./1 mmHg | | | |
| Yield: | 44.5 g | | | |

(2) CH$_3$OC—(CH$_2$)$_4$—CF$_2$—CF—(CH$_2$)$_4$—COCH$_3$
     ‖                       |                    ‖
     O                      CF$_3$             O

Elementary analysis

| | C | H | O | F |
|---|---|---|---|---|
| Calcd. (%) | 47.37 | 5.79 | 16.84 | 30.00 |
| Found (%) | 47.21 | 5.78 | 16.71 | 30.30 |
| Mass: m/e = | 476 (M$^+$) | | | |
| | 434 (M$^+$—CH$_2$COCH$_3$) | | | |
| |                             ‖ | | | |
| |                             O | | | |
| |     +OH | | | |
| |      ‖ | | | |
| | 74 (—CH$_2$—COCH$_3$) | | | |

(3) HOC—(CH$_2$)$_4$—CF$_2$—CF—H
   ‖                    |
   O                  CF$_3$

Elementary analysis

| | C | H | O | F |
|---|---|---|---|---|
| Calcd. (%) | 38.10 | 3.97 | 12.70 | 45.24 |
| Found (%) | 37.92 | 4.11 | 12.80 | 45.17 |
| Mass: m/e = | 252 (M$^+$) | | | |
| | 203 (M$^+$—COOH) | | | |

(4) HOC—(CH$_2$)$_4$—CF$_2$—CF—(CH$_2$)$_4$—COH
   ‖                    |                  ‖
   O                  CF$_3$           O

Elementary analysis

| | C | H | O | F |
|---|---|---|---|---|
| Calcd. (%) | 44.32 | 5.11 | 18.18 | 32.39 |
| Found (%) | 44.03 | 5.11 | 18.27 | 32.59 |

EXAMPLE 3

A 1000 ml quantity of absolute methanol is placed in a reactor equipped with a stirrer and 186 g of 98% cyclododecanone is dissolved thereinto in 20 minutes while maintaining the temperature at 20° C. To the solution are added 10 g of concentrated sulfuric acid and 144.5 g of a 35% aqueous solution of hydrogen peroxide. The mixture is stirred for 60 minutes to yield methoxycyclododecanone peroxide. Absolute methanol (750 ml) is placed in another reactor equipped with a stirrer and filled with a nitrogen gas while retaining the temperature at 20° C. Thereto is added 325 g of ferrous sulfate heptahydrate (FeSO$_4$.7H$_2$O) to prepare a suspension. The methoxycyclododecanone peroxide solution is dropwise added by degrees to the suspension with stirring while maintaining the temperature of the suspension at 20°±2° C. and forcing thereinto a hexafluoropropene gas. After the addition of the solution, the gas is continuously forced into the mixture for 2 hours with stirring until the temperature is elevated to 35° to 40° C. Thereafter the mixture is further stirred for 4 hours without blowing the gas thereinto. The mixture is left to stand until it is brought to room temperature, and a methanol is recovered at an increased temperature (up to 40° C.) and reduced pressure (10 to 15 mmHg). The reaction mixture is separated into an organic layer (upper layer) and an aqueous layer (lower layer). Since the separation is incomplete, 10 g of 50% dilute sulfuric acid and 50 g of ether are added to the mixture and the resulting admixture is fully stirred. Then the upper layer (ether layer) is decanted, washed with water and dried, followed by the distillation of the ether to prepare a mixture of long-chain monobasic acid, long-chain ester of monobasic acid, long-chain dibasic acid and long-chain ester of dibasic acid all of which contain fluorine. The mixture is found to predominantly comprise the following compounds stated below in (1) and (2).

(1) $CH_3OC-(CH_2)_{11}-CF_2-CF-H$
      $\parallel$                    $\mid$
      $O$                           $CF_3$ Elementary analysis (for $C_{16}H_{26}O_2F_6$)

|  | C | H | O | F |
|---|---|---|---|---|
| Calcd. (%) | 52.75 | 7.14 | 8.79 | 31.32 |
| Found (%) | 53.00 | 7.14 | 8.60 | 31.26 |

IR: 1020 cm$^{-1}$ (C—F)
    1100–1230 cm$^{-1}$ (C—F)
    1740 (C=O)

Mass: m/e = 364 (M$^+$)
            333 (M$^+$—CH$_3$O)
            289 (M$^+$—CH$_3$OC—)
                        $\parallel$
                        $O$ (2) $HOC-(CH_2)_{11}-CF_2-CF-H$
      $\parallel$                    $\mid$
      $O$                           $CF_3$ Elementary analysis (for $C_{15}H_{24}O_2F_6$)

|  | C | H | O | F |
|---|---|---|---|---|
| Calcd. (%) | 51.43 | 6.86 | 9.14 | 32.57 |
| Found (%) | 51.20 | 6.85 | 9.04 | 32.91 |

Mass: m/e = 236 (M$^+$)
            187 (M$^+$—COOH)

EXAMPLE 4

A 27 ml quantity of absolute methanol is placed in a reactor cooled to 0° to 5° C. and equipped with a stirrer. Thereto are added 4.6 g (4.7 m mole) of cyclohexanone, 0.16 g of concentrated sulfuric acid and 4.6 g of a 35% aqueous solution of hydrogen peroxide. Then the mixture is stirred for 60 minutes to yield methoxycyclohexanone peroxide.

Absolute methanol (27 ml) is placed in another reactor equipped with a stirrer and filled with a nitrogen gas and is cooled to −40° C. Thereto are added 13 g of ferrous sulfate heptahydrate (FeSO$_4$.7H$_2$O) and 8.2 g of liquefied trifluorochloroethylene. The methoxycyclohexanone peroxide solution is dropwise added by degrees to the mixture while maintaining the temperature of the suspension at −40° C. After the addition of the solution, the stirring is continued at −40° C. for 2 hours and the reaction mixture is left to stand until it is brought to room temperature. The unreacted trifluorochloroethylene and methanol are distilled off and the organic layer is extracted with ether. The extract is washed with acid and water, and dried. Thereafter the ether is distilled off to give 5.0 g of a light yellow oily crude product. Analyses by gas chromatography, mass spectrometry, etc. confirm the production of the following compounds.

(1) HCFClCF$_2$(CH$_2$)$_5$COOCH$_3$
Mass: m/e = 246 (M$^+$)
            215 (M$^+$—CH$_3$O)

187 (M$^+$—CH$_3$OC—)
              $\parallel$
              $O$ $^+$OH
                $\parallel$
74 (CH$_2$—COCH$_3$)

(2) H(CFClCF$_2$)$_2$(CH$_2$)$_5$COOCH$_3$
Mass: m/e = 331 (M$^+$—CH$_3$O)

303 (M$^+$—CH$_3$OC—)
              $\parallel$
              $O$ $^+$OH
                $\parallel$
74 (CH$_2$—C—OCH$_3$)

(3) H(CFClCF$_2$)$_3$(CH$_2$)$_5$COOCH$_3$
Mass: m/e = 447 (M$^+$—CH$_3$O)

$^+$OH
                $\parallel$
74 (CH$_2$—COCH$_3$)

(4) CH$_3$OOC(CH$_2$)$_5$CF$_2$CFCl(CH$_2$)$_5$COOCH$_3$
Mass: m/e = 343 (M$^+$—CH$_3$O)

301 (M$^+$—CH$_2$COCH$_3$)
                $\parallel$
                $O$ $^+$OH
                $\parallel$
74 (CH$_2$—COCH$_3$)

Yield: 0.5 g
(5) CH$_3$OOC(CH$_2$)$_5$(CF$_2$CFCl)$_2$(CH$_2$)$_5$COOCH$_3$
Mass: m/e = 459 (M$^+$—CH$_3$O)

417 (M$^+$—CH$_2$COCH$_3$)
                $\parallel$
                $O$ $^+$OH
                $\parallel$
74 (CH$_2$—COCH$_3$)

Yield: 0.8 g
(6) CH$_3$OOC(CH$_2$)$_5$(CF$_2$CFCl)$_3$(CH$_2$)$_5$COOCH$_3$
Mass: m/e = 575 (M$^+$—CH$_3$O)

533 (M$^+$—CH$_2$COCH$_3$)
                $\parallel$
                $O$

Yield: 1.5 g
(7) CH$_3$OOC(CH$_2$)$_5$(CF$_2$CFCl)$_4$(CH$_2$)$_5$COOCH$_3$
Mass: m/e = 691 (M$^+$—CH$_3$O)

649 (M$^+$—CH$_2$COCH$_3$)
                $\parallel$
                $O$ $^+$OH
                $\parallel$
74 (CH$_2$—COCH$_3$)

Yield: 1.0 g
(8) CH$_3$OOC(CH$_2$)$_5$(CF$_2$CFCl)$_5$(CH$_2$)$_5$COOCH$_3$
Mass: m/e = 807 (M$^+$—CH$_3$O)

765 (M$^+$—CH$_2$COCH$_3$)
                $\parallel$
                $O$

-continued $\overset{+OH}{\underset{\|}{}}$
74 (CH₂COCH₃)

(9) Product having a high boiling point

EXAMPLE 5

A 9 ml quantity of absolute methanol is placed in a reactor cooled to 0° to 5° C. and equipped with a stirrer. Thereto are added 1.47 g of cyclohexanone, 0.05 g of concentrated sulfuric acid and 1.47 g of a 35% aqueous solution of hydrogen peroxide. The mixture is stirred for 60 minutes to yield methoxycyclohexanone peroxide.

Absolute methanol (9 ml) is placed in another reactor equipped with a stirrer and filled with a nitrogen gas and is cooled to −65° C. Thereto are added 4.2 g of ferrous sulfate heptahydrate (FeSO₄.7H₂O) and 2.5 g of liquefied trifluoroethylene. The methoxycyclohexanone peroxide solution is dropwise added by degrees to the mixture at −68° to −65° C. with stirring. After the addition of the solution, the resulting admixture is stirred for 2 hours at −68° C. to −65° C. and then further for 2 hours at −40° C. Thereafter the reaction mixture is left to stand until it is brought to room temperature.

The unreacted trifluoroethylene and methanol are distilled off and the organic layer is extracted with ether. The extract is washed with acid and water, and dried. Then the ether is distilled away to give 1.28 g of a light yellow oily crude product.

Analyses by gas chromatography, mass spectrometry, etc. confirm the production of the following compounds.

(1) HCFHCF₂(CH₂)₅COOCH₃
Mass: m/e = 212 (M⁺)
   181 (M⁺−CH₃O)
   153 (M⁺−CH₃C−)
          $\overset{\|}{O}$
   74 (−CH₂−$\overset{\overset{+OH}{\|}}{C}$OCH₃)

¹⁹FNMR (CH₃COCH₃): (CF₃COOH) 33.0 (CF₂)
   44.0 (CF₂H)
   119.5 (CF)

(2) H(CFHCF₂)₂(CH₂)₅COOCH₃
Mass: m/e = 294 (M⁺)
   263 (M⁺−CH₃O)
   235 (M⁺−CH₃C−)
          $\overset{\|}{O}$
   74 (−CH₂−$\overset{\overset{+OH}{\|}}{C}$OCH₃)

(3) CH₃OOC(CH₂)₅CF₂CFH(CH₂)₅COOCH₃
Mass: m/e = 340 (M⁺)
   298 (M⁺−CH₂COCH₃)
          $\overset{\|}{O}$ -continued 74 (−CH₂−$\overset{\overset{+OH}{\|}}{C}$OCH₃)

(4) CH₃OOC(CH₂)₅(CF₂CFH)₂(CH₂)₅COOCH₃
Mass: m/e = 422 (M⁺)

380 (M⁺−CH₂COCH₃)
          $\overset{\|}{O}$ 74 (−CH₂−$\overset{\overset{+OH}{\|}}{C}$OCH₃)

(5) Products having a high boiling point

EXAMPLE 6

A 9 ml quantity of absolute methanol is placed in a reactor cooled to 0° to 5° C. and equipped with a stirrer. Thereto is added 1.47 g of cyclohexanone and the mixture is stirred for 60 minutes to yield methoxycyclohexanone peroxide.

Absolute methanol (9 ml) is placed in another reactor equipped with a stirrer and filled with a nitrogen gas and is cooled to −30° C. Thereto are added 4.2 g of ferrous sulfate heptahydrate (FeSO₄.7H₂O) and 2.4 g of liquefied hexafluorobutadiene. The methoxycyclohexanone peroxide solution is dropwise added by degrees to the mixture at −30° C. with stirring. After continued stirring for 2 hours at −30° C. subsequent to the addition of the solution, the reaction mixture is left to stand until it is brought to room temperature.

The unreacted hexafluorobutadiene and methanol are distilled off and then the organic layer is extracted with ether. The extract is washed with acid and water, and dried. Subsequently the ether is distilled away to give 1.5 g of a white wax-like crude product.

Analyses by gas chromatography, mass spectrometry, etc. confirm that a carboxylic acid containing hexafluorobutadiene as fluorine-containing functional groups and the methyl ester thereof are present in the crude product. The crude product is found to predominantly comprise the following compounds.

(1) H(CF₂−CF)(CH₂)₅COOCH₃
         |
         CF
         $\|$
         CF₂

CH₃COO(CH₂)₅(CF₂−CF)(CH₂)₅COOCH₃
         |
         CF
         $\|$
         CF₂

(2) H(CF₂CF=CFCF₂)(CH₂)₅COOCH₃
CH₃COO(CH₂)₅(CF₂CF=CFCF₂)(CH₂)₅COOCH₃

(3) Products having a high boiling point

We claim:
1. A fluorine-containing compound of the formula

R₁—A—R₂ wherein A is

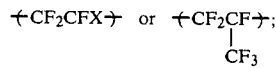 or 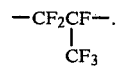
$R_1$ and $R_2$ are each hydrogen or $HOOC$-$(CH_2)_5$, while $R_1$ and $R_2$ may not be hydrogen at the same time; X is hydrogen or halogen.
2. A fluorine-containing compound as defined in claim 1 in which A is
$$-CF_2CF-.$$
$$\phantom{-CF_2C}|$$
$$\phantom{-CF_2C}CF_3$$
3. A fluorine-containing compound as defined in claim 1 in which $R_1$ and $R_2$ are both $HOOC-CH_2)_5$.
* * * * *